United States Patent [19]
Bills

[11] Patent Number: 5,453,270
[45] Date of Patent: Sep. 26, 1995

[54] PHARMACEUTICAL COMPOSITION AND METHOD FOR HYPERMETABOLIC WEIGHT LOSS

[75] Inventor: Nathan Bills, Elkhorn, Nebr.

[73] Assignee: Hypermetabolic Therapies, Inc., Corvallis, Oreg.

[21] Appl. No.: 25,623

[22] Filed: Mar. 2, 1993

Related U.S. Application Data

[63] Continuation-in-part of Ser. No. 859,831, Mar. 30, 1992, abandoned.

[51] Int. Cl.$^6$ .......................... A61B 19/00; A01N 63/02; C12N 11/14; C12N 5/00

[52] U.S. Cl. .................. 424/93.7; 128/897; 128/898; 128/899; 424/93.1; 424/94.6; 424/423; 424/484; 424/574; 435/174; 435/176; 435/177; 435/178; 435/180; 435/182; 435/240.22; 514/909

[58] Field of Search ................ 435/240.22, 174, 435/176, 177, 178, 180, 182; 424/574, 934, 93.1, 93.7, 94.6, 423, 484, 574; 514/909; 128/897, 898, 899; 604/892.1

[56] References Cited

U.S. PATENT DOCUMENTS

| | | | |
|---|---|---|---|
| 4,352,883 | 10/1982 | Lim | 435/178 |
| 4,661,458 | 4/1987 | Berry | 435/284 |
| 5,055,460 | 10/1991 | Friedlander | 514/161 |
| 5,073,491 | 12/1991 | Familletti | 435/240.22 |

OTHER PUBLICATIONS

Lacy et al., "Maintenance of Normoglycemia in Diabetic Mice by Subcutaneous Xenografts of Encapsulated Islets" Science 254:1782, 1991.
Lanza et al., "Xenotransplantation of Canine, Bovine, and Porcine Islets in Diabetic Rate Without Immunosuppression" Proc. Natl. Acad. Sci. USA 88:11100, 1991.
Casteilla et al., "Stable Expression of Functional Mitochondrial Uncoupling Protein in Chinese Hamster Ovary Cells" Proc. Natl. Acad. Sci. USA 87:5124, 1990.
Rehnmark et al., "α- and β-Adrenergic Induction of the Expression of the Uncoupling Protein Thermogenin in Brown Adipocytes Differentiated in Culture" J. Biol. Chem. -:16464, 1990. [Rehnmark et al. I].
Rehnmark et al., "Brown Adipocytes Differentiated in Vitro Can Express the Gene for the Uncoupling Protein Thermogenin: Effects of Hypothyroidism and Norepinephrine" Exp. Cell Res. 182:74, 1989. [Rehnmark et al. II].
Néchad, "Development of Brown Fat Cells in Monolayer Culture" Exp. Cell Res. 149:119, 1983.
Cannon et al., "The Biochemistry of an Inefficient Tissue: Brown Adipose Tissue" Essays Biochem. 20:110, 1985.
Prusiner et al., "Oxidative Metabolism in Cells Isolated from Brown Adipose Tissue" Eur. J. Biochem. 6:15, 1968.
Kitano et al., "Hollow Fiber Enzyme Reactors" Trends Biotech. 2:5, 1984.
Cassard et al., "Human Uncoupling Protein Gene: Structure, Comparison With Rat Gene, and Assignment to the Long Arm of Chromosome 4" J. Cellular Biochem. 43:255, 1990.
Bouillaud et al., "Detection of Brown Adipose Tissue Uncoupling Protein mRNA in Adult Patients by a Human Genomic Probe" Clin. Sci. 75:21, 1988.
Nyberg et al., "Hepatocyte Culture Systems for Artificial Liver Support: Implications for Critical Care Medicine (Bioartificial Liver Support)" Critical Care Med. 20:1157, 1992.

*Primary Examiner*—John W. Rollins
*Assistant Examiner*—Deborah K. Ware
*Attorney, Agent, or Firm*—Jeffrey B. Oster

[57] ABSTRACT

There is disclosed a pharmaceutical composition and method for metabolic consumption of calories and weight loss. The pharmaceutical composition is a culture of brown adipose cells, preferably encapsulated in a porous growth matrix, and a semipermeable membrane encapsulating the porous matrix wherein the semipermeable membrane has a molecular weight cutoff of at least 10,000 daltons and, preferably, a lipoprotein lipase embedded therein. Further disclosed is a pharmaceutical composition for metabolizing fatty acids into carbon dioxide, water and heat including a mammalian cell stably transfected with a DNA sequence coding for a mammalian UCP polypeptide, wherein the transfected mammalian cell transcribes and translates UCP polypeptide. Also disclosed is a pharmaceutical composition for metabolizing fatty acids into carbon dioxide, water and heat including a cDNA sequence encoding a mammalian UCP sequence, wherein the cDNA sequence is taken up into a hosts cell, in vivo, and is translated into UCP polypeptide, causing uncoupling of oxidative metabolism. The present invention provides a pharmaceutical composition for metabolizing fatty acids into carbon dioxide, water and heat which includes a culture of allogeneic brown fat cells, wherein the brown fat cells are proliferated ex vivo.

9 Claims, 3 Drawing Sheets

PHARMACEUTICAL COMPOSITION AND METHOD FOR HYPERMETABOLIC WEIGHT LOSS

CROSS-REFERENCE TO RELATED APPLICATION

This application is a continuation-in-part of U.S. patent application 07/859,831 filed on Mar. 30, 1992, now abandoned.

TECHNICAL FIELD OF THE INVENTION

The present invention relates to a device, pharmaceutical composition, therapeutic agent and therapeutic method for metabolic consumption of calories leading to weight loss for a treated individual. The pharmaceutical composition comprises brown fat tissue or cells transfected with a cDNA encoding mitochondrial uncoupling protein.

BACKGROUND OF THE INVENTION

Weight loss methods and techniques have involved some form of reducing caloric consumption or increasing exercise output to result in utilization of fat stores (e.g., triglycerides) as an energy source. Reducing consumption-type therapies have included various sympathomimetic agents, such as amphetamines and derivatives to increase metabolic rate while reducing the individuals appetite in an effort to reduce caloric consumption.

Numerous attempts have been made, with varying degrees of success and varying degrees of risk to the individual, to reduce body weights of an individual through reduction of fat stores. One general problem with most weight loss programs or therapies is that starving or reducing caloric intake results in metabolism of both fat stores and muscle mass as energy sources for body metabolism. Therefore, one goal of weight loss therapies is to be able to reduce body fat stores while not reducing muscle mass.

There are two types of mammalian fat cells, white fat cells and brown fat cells. Brown fat cells are characterized by the presence of numerous mitochondria that have unique metabolic capacity. Brown fat mitochondria completely catabolize or oxidize fatty acids as a fuel substrate without utilizing the energy source. More specifically, brown fat mitochondria oxidize fatty acids into the metabolic products carbon dioxide and water and heat (energy). Therefore there is a net oxidation of fuel with no use or storage of energy produced except in the form of heat (Cannon et al., *Essays Biochem.* 20:110, 1985).

The primary function of brown fat in mammals is to keep the mammal warm. Mammals have varying amounts and location of brown fat. Infants have larger areas of brown fat than adults.

Brown adipose tissue (BAT) is primarily concerned with maintenance of homeothermy through non-shivering thermogenesis (Cannon et al., *Essays Biochem.* 20:110, 1985). BAT has a high degree of vascularity, abundant mitochondria and high cytochrome concentrations in its mitochondria. Humans have brown fat located primarily in the back of the neck and subscapular regions. BAT is also located in the thorax, around the pericardium and sinoatrial node, along the aorta, around adrenal glands, and around sympathetic ganglia in the abdomen (Smith et al., *Physiol. Rev.* 49:330, 1969). With increasing age or obesity, brown fat becomes paler in color and more difficult to distinguish from white adipose tissue. White adipose tissue normally represents 15–25% of body weight and may reach up to 60% of body weight in massive obesity. Generally, BAT usually comprises less than 1% of total adult body weight.

Brown adipocytes (BA) contain multilocular lipid droplets and numerous mitochondria. BAT contains an abundant capillary plexus supplied by lobular arteries and drained by lobular veins. Further, BAT contains direct arteriovenous anastomoses, similar to those seen in liver (Nnodim et al., *Am. J. Physiol.* 182:283, 1988). BAT and blood vessels supplying BAT are innervated by sympathetic nerves as the only innervation from the autonomic nervous system (Cottle et al., *Histochem. J.* 17:1279, 1985).

White adipose tissue exports lipid to other tissues on demand. BAT oxidizes both endogenous and exogenous fatty acids. Therefore, BAT's physiologic role includes temperature regulation and possible maintenance of energy balance. When BAT was surgically removed from Osborne-Mendel or Zucker rats, the animals demonstrated increased body fat accumulation. Thus when functional BAT is reduced there is increased body fat accumulation. Decreased BA thermogenesis leads to altered energy balance and increased white fat deposition.

Brown fat cells uniquely contain and preferentially express an uncoupling protein called thermogenin, mitochondrial uncoupling protein or UCP. UCP uncouples the usual process of catabolism and storage of energy in the form of adenosine triphosphate (ATP) (Cannon et al., *FEBS Lett.* 150: 129, 1982). UCP is a 32 kD protein found in the inner membrane of BA mitochondria. UCP serves as a proton channel to decrease the transmembrane proton gradient which drives the electron transport system (Nicholls et al., *Biochem. Biophys. Acta* 549:1, 1979). This uncouples oxidative phosphorylation of ATP from oxidation of fat fuel substrates and increases the rate of oxidation. Norepinephrine activates uncoupling of oxidative phosphorylation mediated by UCP. Norepinephrine is thought to exert its effect through cAMP-activated hydrolysis of triacylglycerols to release free fatty acid. Free fatty acids mimic the effect of norepinephrine and are themselves potent uncouplers of oxidative phosphorylation. Purine nucleotides are considered negative modulators (Jezek et al., *Fed Eur. Biochem.* 243:1147, 1989).

UCP is expressed in response to external stimuli of cold-acclimation in hamsters and rats. Based upon gene expression in the mouse, four hours of cold stress to the whole animal led to a seven-fold increase in UCP mRNA. Administration of norepinephrine also increased UCP mRNA to a lesser extent. UCP expression can also be induced in preadipocytes grown in culture. UCP mRNA translation was maximally stimulated by Norepinephrine when the cells were in confluence and in the presence of insulin or thyroid hormones (e.g., T3, T4, etc.). See, for example, Rehnmark et al., *Exp. Cell Res.* 182:75, 1989 and Rehnmark et al., *J. Biol. Chem.* 265:16464, 1990.

UCP is a proton/anion transporter found in the inner mitochondrial membrane of brown adipocytes. The mouse, rat, hamster and human genes encoding for UCP have been isolated and sequenced. UCP gene expression is controlled at the level of transcription by signals that are activated after stimulation of brown adipocytes by norepinephrine. The UCP sequence is strongly homologous to several other ubiquitous mitochondrial carriers, such as ANT (adenine nucleotide translocator) and a mitochondrial phosphate carrier. Jacobsson et al. (*J. Biol. Chem.* 260:16250, 1985) reported an isolation of a murine cDNA clone derived from brown adipose tissue mRNA. The cDNA was cold-inducible. No sequence data were provided. Bouillard et al. (*J. Biol. Chem.* 261:1487, 1986) reported a complete cDNA sequence and corresponding protein sequence for rat UCP. The rat UCP gene has no N-terminal signal extension. Rat UCP has a calculated molecular weight of 33,042 daltons and 306 amino acid residues. Ridley et al. (*Nucleic Acids Res.* 14:4025, 1986) also reports the cDNA and corresponding protein sequence for rat UCP as a 306 amino acid polypeptide. Ridley et al. state that the rat UCP cDNA sequence is 91.5% homologous to hamster UCP on the protein level. Kozak et al. (*J. Biol. Chem.* 263:12274, 1988) report two cDNA sequences for murine UCP. The polypeptide has six α-helical hydrophobic transmembrane domains, each encoded by an exon.

In view of the function of BAT to oxidize fuel substrates and BA to be regulated by norepinephrine, free fatty acids and other metabolic regulators, there is a need in the art to design a system to utilize the unique metabolic properties of BA to tip the metabolic balance toward white adipose tissue catabolism while preserving muscle mass. The following invention was made to fulfill this need.

SUMMARY OF THE INVENTION

The present invention relates to a device, pharmaceutical composition and method for metabolizing fatty acids into water, carbon dioxide and heat and thereby reducing an individual's white adipose tissue mass without effecting muscle mass. More particularly, the inventive device is an extracorporeal device for oxidizing fatty acids comprising a semipermeable membrane having a first and a second side and having a molecular weight cutoff of at least 10,000 daltons, an oxidizing component located adjacent to the first side of the semipermeable membrane comprising an enzyme system with necessary cofactors, brown fat mitochondria or whole cell cultures of brown adipose cells of any species or cells transfected with a construct comprising a UCP DNA sequence and an appropriate mammalian promoter sequence (e.g., MMTV, SV40, CMV intermediate early, etc.), wherein the oxidizing component is capable of oxidizing fatty acids into carbon dioxide, water and heat, and a means for circulating blood from the individual to the second side of the semipermeable membrane for triglyceride hydrolysis and diffusion of free fatty acids to the first side of the semipermeable membrane for oxidation of fatty acids and returning treated blood to the individual. Preferably, the oxidizing component comprises a culture of brown fat cells or other eukaryotic cells transfected with a gene encoding an uncoupling protein thermogenin in an expression vector. Preferably the semipermeable membrane has a lipoprotein lipase (EC 3.1.1.34) embedded therein.

The present invention further provides a pharmaceutical composition for metabolizing fatty acids into carbon dioxide, water and heat comprising a culture of brown fat cells or UCP-transfected cells encapsulated in a porous growth matrix and having a semipermeable membrane encapsulating the porous growth matrix. The semipermeable membrane has a molecular weight cutoff of at least 10,000 daltons and, preferably, a lipoprotein lipase embedded therein. Preferably, the semipermeable membrane comprises a tubular membrane having two ends, filled with brown fat cells in the porous growth matrix and sealed at both ends prior to subcutaneous, intramuscular or intraperitoneal implantation. Preferably the porous growth matrix comprises alginate beads or another complex polysaccharide porous matrix suitable for cellular growth and metabolism.

The present invention further provides a pharmaceutical composition for metabolizing fatty acids into carbon dioxide, water and heat comprising a mammalian cell stably transfected with a DNA sequence coding for a mammalian UCP polypeptide, wherein the transfected mammalian cell transcribes and translates UCP polypeptide. Preferably, the transfected mammalian cell further comprises a cDNA sequence that confers antibiotic sensitivity to the mammalian cell as a "suicide gene" mechanism to remove the transformed mammalian cell from the treated individual. Most preferably, the antibiotic is gancyclovir.

The present invention further provides a pharmaceutical composition for metabolizing fatty acids into carbon dioxide, water and heat comprising a cDNA sequence encoding a mammalian UCP sequence in combination with appropriate regulatory [please specify examples] and promoter sequences, wherein said cDNA sequence is taken up into a hosts cells, in vivo, and is translated into UCP polypeptide, causing uncoupling of oxidative metabolism.

The present invention further provides a pharmaceutical composition for metabolizing fatty acids into carbon dioxide, water and heat comprising a culture of allogeneic brown fat cells, wherein the brown fat cells were proliferated ex vivo.

Further still, the present invention provides a method for effecting weight loss for an individual, wherein the weight loss is due to loss of white adipose tissue, with minimal loss of muscle mass, wherein the method for effecting weight loss comprises administration of an effective amount of a pharmaceutical composition described herein in sufficient amounts to metabolize at least 55 calories or 65 g per day of fatty acids.

DETAILED DESCRIPTION OF THE INVENTION

Figure 1:
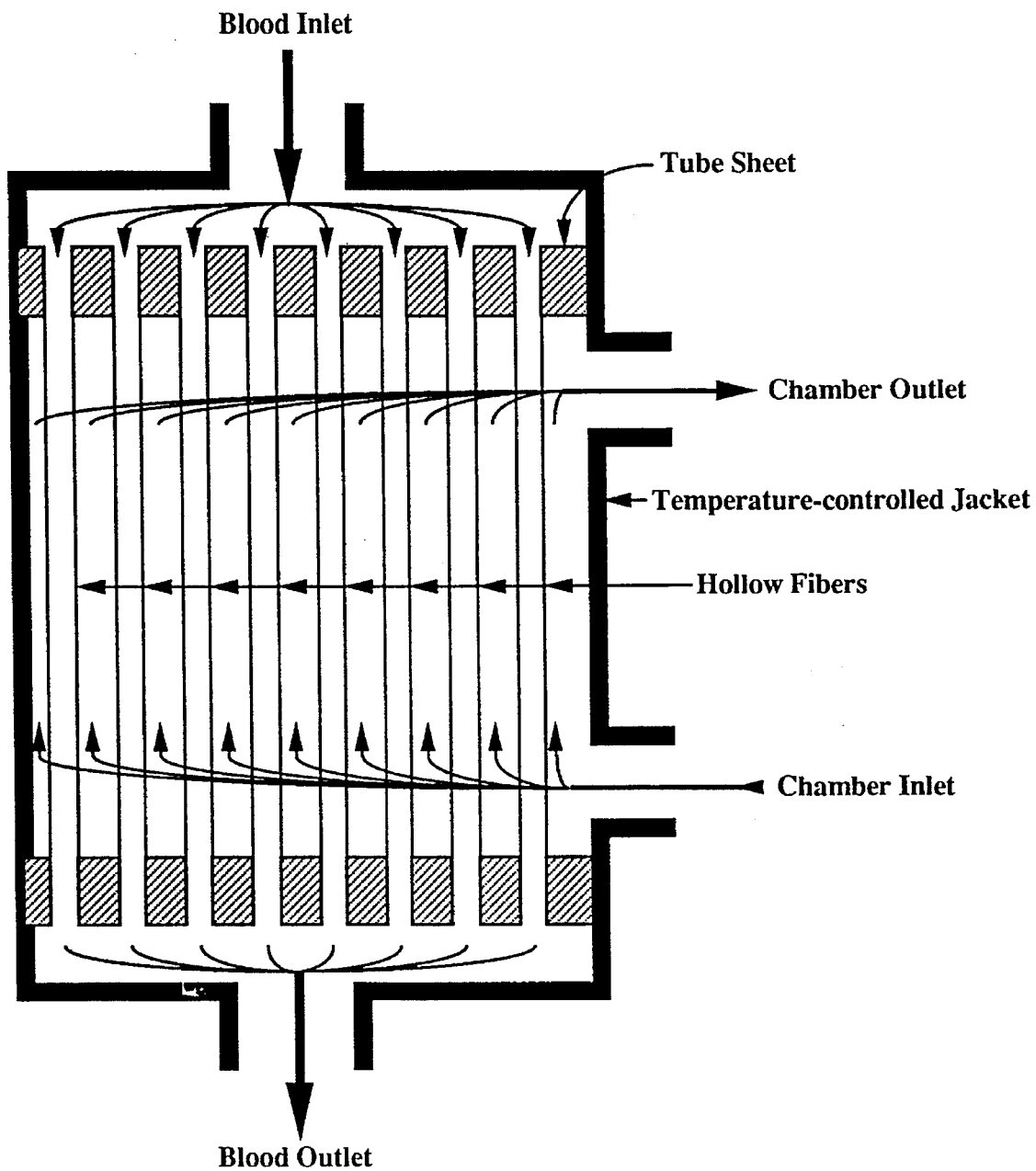
FIG. 1 is a schematic diagram of an extracorporeal device for oxidizing fatty acids, comprising a kidney dialysis machine as a means for circulating blood from an individual to the first side of the semipermeable membrane and for returning treated blood back to the individual. The cell chamber comprises a plurality of "hollow fibers" comprising semipermeable membranes encapsulating brown adipose cell cultures arranges to allow blood to circulate around the hollow fibers.
Figure 2:
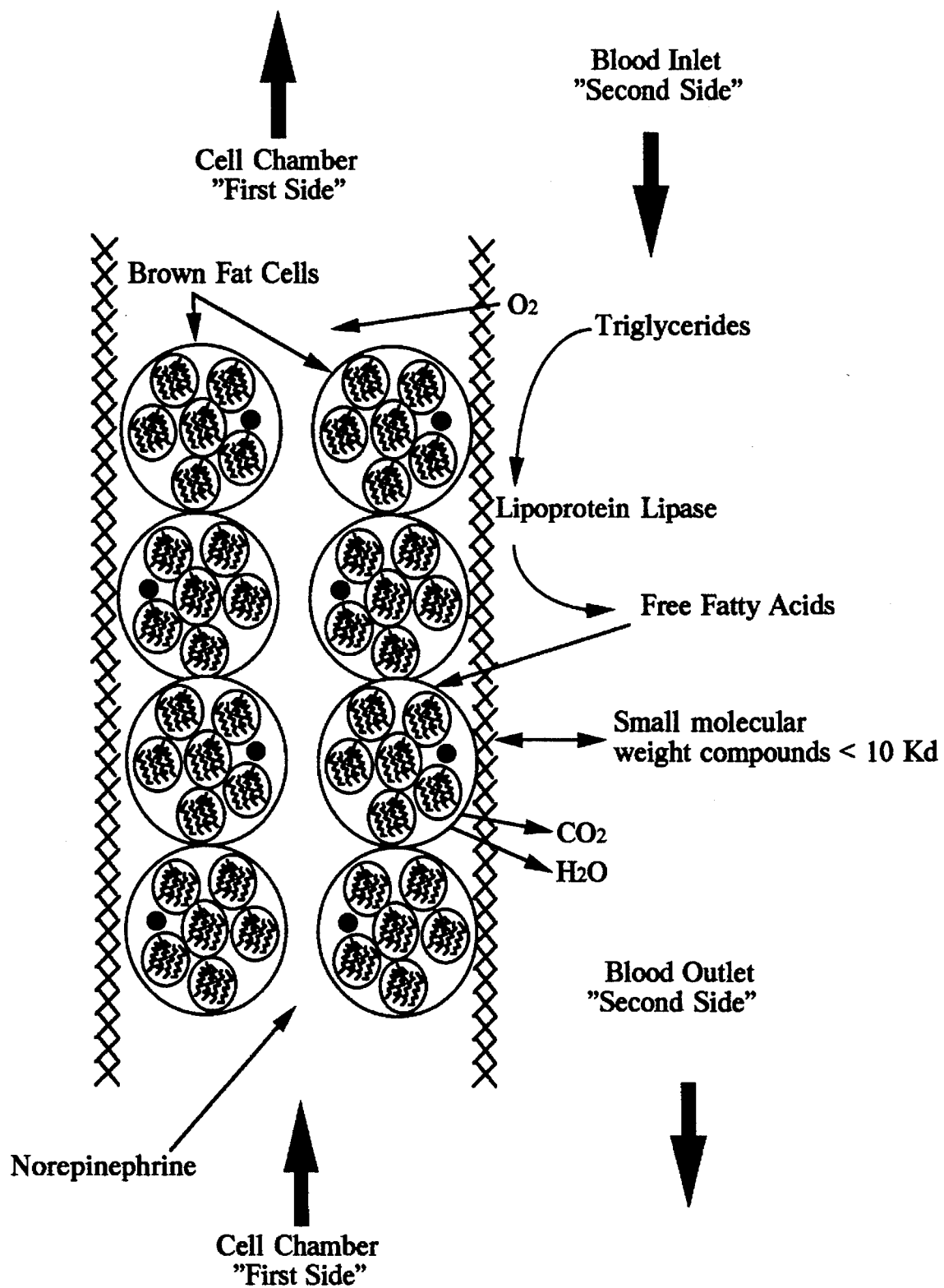
FIG. 2 provides a more detailed view of the cell chamber of an extracorporeal device showing metabolic and kinetic pathways of various biochemicals during operation of the extracorporeal device.
Figure 3:
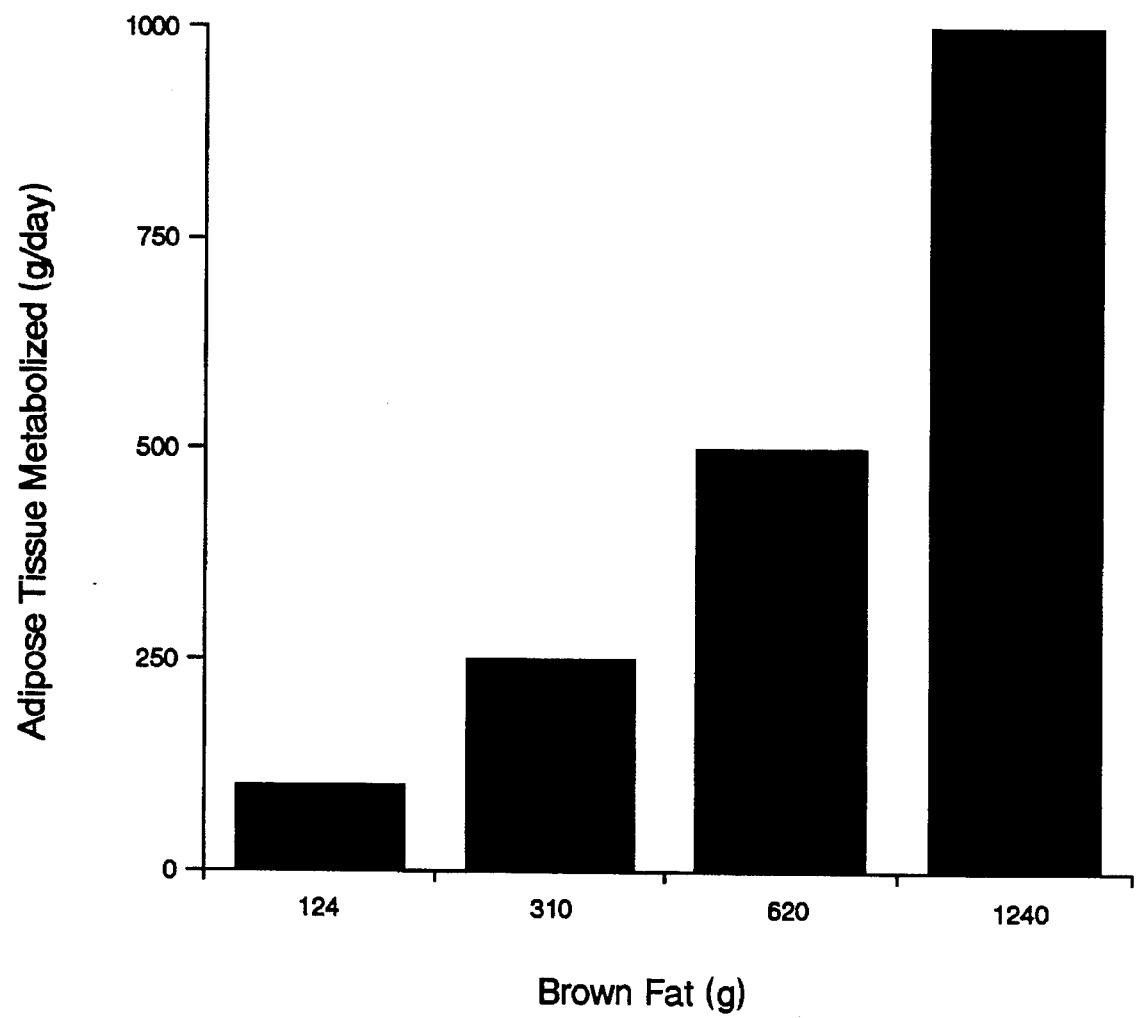
FIG. 3 is a graph of the amount of brown fat cells needed to metabolize a certain amount of calories of grams of fat per day (24 hour period) when administered as a pharmaceutical composition. Approximately 1.24 g of brown adipose cells will metabolize about 1 g of white adipose tissue per day.

The inventive pharmaceutical composition for metabolizing fatty acids into carbon dioxide, water and heat comprises a culture of brown adipose cells encapsulated in a semipermeable membrane. Preferably, the culture of brown adipose cells are grown in a monolayer culture prior to encapsulation. Preferably, the culture of brown adipose cells is first encapsulated in a porous growth matrix, which, in turn, in then encapsulated by the semipermeable membrane.

Sources of Brown Adipose Cells

The brown adipose tissue can be obtained from many mammalian sources. Preferably, brown adipose tissue is cultured from the patient so that the cells can be grown and added to the pharmaceutical composition in a form of an autologous transplantation. Other human sources of brown adipose tissue are appropriate without regard to matching of the major histocompatibility antigens due to immunoisolation afforded by the semipermeable membrane. Other mammalian sources of brown adipose tissue are also appropriate, particularly from those species inhabiting polar climates (Lacey et al., *Science* 254:1782; Lanza et al., *Proc. Natl. Acad. Sci.* USA 88:11100).

The pharmaceutical composition encapsulates the brown adipose cells in a semipermeable membrane such that larger proteins and immune cells from the host individual cannot contact the implanted brown adipose cells. Preferably, brown adipose cells are first encapsulated in a porous growth matrix, such as an alginate porous matrix, and then further encapsulated in the semipermeable membrane. However, fatty acids, carbon dioxide, water and other metabolic byproducts and essential nutrients can freely migrate across the semipermeable membrane and throughout the porous growth matrix.

Preparation of Brown Adipose Cells for Encapsulation

In order to prepare the brown adipose cells for immobilization in a porous growth matrix, cells are obtained by isolating brown adipose precursor cells from inter scapular brown adipose tissue of young mammals. Inter scapular brown adipose tissue is dissected out, under sterile conditions, the tissue is cut into small pieces and incubated in isolation buffer (123 mM NaCl, 5 mM KCl, 1.3 mM $CaCl_2$, 5 mM glucose, 1.5% crude bovine serum albumin and 100 mM HEPES, adjusted to pH 7.4 with NaOH; 0.2% (w/v) collagenase added and sterile filtered through 0.45 μm and 0.22 μm prior to use) in siliconized glass vials at 37° C. in a shaking water bath. During incubation, each vial is shaken vigorously, such as by vortex, to separate the tissue into a cellular suspension.

The tissue remnants are filtered through a 250 mm nylon screen. Mature adipocytes and fat droplets from broken cells can float to the surface after about 30 min and can be collected and discarded. The remaining intact cells are collected and filtered through a 25 mm nylon screen to remove aggregates. The collected cells are washed and centrifuged, resuspended in culture medium and inoculated into flasks for growth. Brown adipose cells can be cultured in common culture media for cell culture. One example of appropriate media is Dulbecco's modified Eagle's medium supplemented with 10% fetal calf serum, 4 nM insulin, 10 mM HEPES, antibiotics (e.g., 50 IU Penicillin and 50 μg streptomycin) and 25 μg sodium ascorbate. Other appropriate media include RPMI 1640, Minimal Essential media, Dulbecco's and Iscove's Modified Dulbecco's Medium.

Encapsulating Brown Adipose Cells or UCP-Transfected Cells in a Porous Growth Matrix Procedures for encapsulating cells in the porous growth matrix for further growth and metabolism of the cells has been described in, for example, U.S. Pat. 5,073,491, the disclosure of which is incorporated by reference herein. Briefly, brown adipose cells or UCP-transfected cells are obtained and isolated by procedures described herein. Once cultures of brown adipose cells or UCP-transfected cells are obtained, they are grown in suspension in a liquid growth medium such as RPMI 1640, Dulbeccos or Minimal Essential Medium. Culture medium may be supplemented with up to 10% heat inactivated fetal calf serum, however, the cells are washed several times with medium or Hanks balance salt solution to remove most proteins from the calf serum. After washing, the cells are suspended in media to encapsulate them in the porous growth matrix.

Preferably the porous growth matrix comprises alginate. The term "alginate" refers to any of the conventional salts of algin, a polysaccharide of marine algae which may be polymerized to form a porous matrix. Algin salts include, but are not limited to, any metal salt such as sodium magnesium, potassium, etc. Preferably, the alginate porous matrix includes, but is not limited to, a polymeric composition of gluronic and mannuronic acids and the material has a relatively low viscosity.

Other polymerization materials that can form the porous growth matrix include, for example, gelatin obtained from animal (i.e., bovine or swine) skin, carageenin obtained by extraction of various red seaweeds, and agarose which is a natural gelling fraction of a polysaccharide complex extracted from agarocytes of algae, such as Rhodophyceae. The preferred polysaccharide polymeric material is alginate. Alginate polymerizes from a liquid solution when exposed to polyvalent cations to form a porous matrix that can entrap cells and provide a stable growth chamber to allow metabolism or even hypermetablism of entrapped brown adipose cells and allow for entry of nutrients and fatty acid fuel and exiting of metabolic by-products $CO_2$, water and heat.

The alginate porous growth matrix is obtained by converting water soluble sodium alginate to insoluble calcium alginate in accordance with procedures well known in the art. See, for example, Knorr et al., *Food Technol.* 39:135, 1985; Chibata et al., *Ann. Rev. Biophys. Bioengin.* 10:197, 1981; and Shiria et al., *J. Appl. Microbiol. Biotechnol.* 26:495, 1987.

An alginate solution is prepared by mixing sodium alginate in a growth medium (containing cultured brown adipose cells) and a NaCl solution. A preferred alginate solution contains about 0.85% to about 4% (w/v) alginate. A most preferred solution contains about 1.0% (w/v) alginate. The alginate solution, containing the suspended cultured brown adipose cells, is pumped through a tube, preferably a 5 mm diameter tube, and dripped into a growth chamber of a bioreactor containing a calcium solution. Preferably, the calcium solution contains about 50 mM $CaCl_2$ and about 0.1M NaCl. The pH of the solutions should be in the range of 6.7–7.3. This will form alginate beads of approximately 8 mm diameter containing the brown adipose cells entrapped within. Normally the cells will grow first toward the periphery of the beads, where there is the greatest concentration of oxygen and nutrients.

Preparation of a Stably Transfected Mammalian Cell

The present invention further provides a pharmaceutical composition for metabolizing fatty acids into carbon dioxide, water and heat comprising a mammalian cell stably transfected with a DNA sequence coding for a mammalian UCP polypeptide, wherein the transfected mammalian cell transcribes and translate UCP polypeptide. The cDNA sequence encoding a human UCP polypeptide has been described in Bouillaud et al. *Clin. Sci.* 75:21–27. 1988 and in Cassard et al. *J. Cell Biochem.* 43:255–264, 1990). One can obtain a cDNA sequence and even a genomic sequence of human UCP through standard polymerase chain reaction (PCR) techniques. The cDNA sequence or genomic DNA sequence encoding a UCP polypeptide is inserted into the genome of a mammalian cell growing in culture. Preferably, the mammalian cell is a fibroblast cell line obtained from the individual to be treated and cultured ex vivo. Other suitable cells include, for example, hepatocytes preadipocytes, adipocytes, myoblasts, myocytes, endothelial cells, and bone marrow stromal cells from the individual to be treated or syngeneic to the individual. The cDNA sequence is inserted into the mammalian cell through any one of a number of techniques, such as transfection, electroporation, or microinjection. In any of the insertion techniques, the cDNA or genomic DNA sequence will first be inserted into a stable expression vector. For example, a pECE expression vector consists of the SV40 early promoter (Ellis et al. *Cell* 45:721, 1986) upstream of the gene for the heterologous protein (e.g., UCP). A region of a cDNA coding for human or mammalian UCP is inserted into an expression vector by taking a restriction fragment digest of the cDNA wherein the restriction fragment comprises at least the entire polypeptide coding region. For example, in the rat UCP cDNA sequence, a BamHI or Bg/I digestion will provide a fragment containing the entire coding region.

For transient expression into a cell, a UCP DNA sequence (or inverted UCP DNA sequence) comprising at least the coding region for a UCP polypeptide in an expression vectors introduced into the cell by, for example, calcium phosphate precipitation with glycerol shock as described by Ebina et al. (*Proc. Natl. Acad. Sci. USA* 82:8014, 1985). Stable cell lines containing the UCP DNA sequence are established by co-transfecting the mammalian cells with the UCP cDNA sequence in a mammalian expression vector and an expression vector to provide stability for the transfected genome, such as pSV2neo DNA (Southern and Berg, *Mol. Appl. Genetics* 1:327, 1982), currently available from Immunex (Seattle, Wash.). The cells are exposed to the expression vector containing the UCP DNA sequence for at least 12 hrs and preferable for 18 to 24 hrs. The cells are washed (possibly first treated with trypsin to remove adherent cells from their plates) and replated with culture medium supplemented with glutamine (10 mM) and at least 10% (v/v) fetal calf serum. An antibiotic (preferably geneticin at about 600 μg/ml) is added, but other antibiotics, such as penicillin/streptomycin, or gentamycin, can be used. After a period of incubation of from one to three weeks (with at least thrice week changing of culture medium) independent colonies are picked on paper disks saturated with trypsin if the cells are adherent. Each colony is transferred to a well plate to observation of its colony characteristics.

Cell transfection could also be achieved by electroporation. Briefly, cultured cells are harvested (after first being treated with trypsin if adherent), and then suspended in an electroporation buffer. A DNA construct comprising a DNA sequence encoding a UCP polypeptide and containing expression and regulatory vectors is placed into sterile electroporation chambers. A controlled unidirectional pulse is applied to the chamber. The electroporated cells are replated into post-electroporation cultures. The electroporation technique is described in, for example, Andreason and Evans, *BioTechniques* 6:650, 1988; Toneguzzo et al., *Mol. Cell. Biol.* 6:703, 1986; and Tur-Kaspa et al., *Mol. Cell. Biol.* 6:716, 1986.

Candidate cell types for transient transfection are cells from the individual to be treated cultured ex vivo, including fibroblasts, hepatocytes, preadipocytes, myoblasts, myocytes, endothelial cells, bone marrow stromal cells, and combinations thereof in fixed culture. Candidates for stably transfected cells include the proceeding cell types and xenogenic cells of the proceeding cell types and any transformed mammalian cell line, including 3t3 Ll cells and NIH 3T3 Ras cells.

Preferably, the transfected mammalian cell further comprises a cDNA sequence that confers antibiotic sensitivity to the mammalian cell as a "suicide gene" mechanism to remove the transformed mammalian cell from the treated individual. Most preferably, the antibiotic is gancyclovir. The thymidine kinase gene of herpes simplex virus (Colbere-Garapin et al., *Proc. Natl. Acad. Sci. USA* 76:3755,, 1979) confers sensitivity to acyclovir or gancyclovir (Darby et al., *Nature* 289:81,198 I). This gene can be introduced into cells via electroporation (described herein), by means of a viral transfection vector, or by microinjection as described by Tabin et al. (*Mol. Cell. Biol.* 2:426, 1982) or Dagher et al. (*Exp. Cell Res.* 198:36, 1992).

The present invention further provides a pharmaceutical composition for metabolizing fatty acids into carbon dioxide, water and heat comprising a cDNA sequence encoding a mammalian UCP sequence, wherein said cDNA sequence is taken up into a hosts cells, in vivo, and is translated into UCP polypeptide, causing uncoupling of oxidative metabolism. For example, an adenovirus vector containing the lacZ gene was successfully introduced into the lumen of intact human umbilical veins and expression of these genes in epithelial cells were verified (Lemarchan et al., *Proc. Natl. Acad. Sci. USA* 89:6482, 1992). Replication deficient, recombinant adenovirus vectors were also used to transfer human αl-antitrypsin gene into rat hepatocytes via intraportal injection. Expression of this gene was detected for at least four weeks (Jaffe et al., *Nature Genetics* 1:372, 1992). A similar adenovirus vector containing the UCP gene with or without a thymidine kinase gene would be introduced into the intraportal vein and expressed in the liver of the individual to be treated. Expression of UCP would continue for a considerable period of time and result in uncoupling of oxidative phosphorylation and cause consumption of metabolic substrates.

Formation of the Pharmaceutical Composition

The brown adipose cells or UCP-transfected cells grown in the porous growth matrix are added to hollow fibers, wherein the hollow fibers comprise the semipermeable membrane. The semipermeable membrane can be any such device allowing free diffusion of molecules having a molecular weight below about 10,000 daltons but preventing migration of cells and larger proteins across the semipermeable membrane. A hollow fiber semipermeable membrane can be formed, for example, by using a wet-dry spinning technique as described in Cabassom Hollow Fiber Membranes, vol 12, page 492 in *Kirk-Othmer Encyclopedia of Chemical Technology*, Wiley, New York ed. 3, 1980. An acrylic copolymer (e.g., poly(acrylonitrile-co-vinyl chloride) $M_n$ ~100,000, $M_w$ ~300,000 as measured by size-exclusion chromatography) is dissolved in dimethylsulfoxide (12.5% w/w). The acrylic copolymer solution is pumped through an outer tube of a spinneret and water is pumped through the inner tube. Type I hollow fibers are extruded into the water through an air gap, resulting in an fenestrated outer wall. Type II fibers are made in an analogous fashion, except the air gap is replaced with a humidified atmosphere.

Brown adipose cells or UCP-transfected cells in porous grow matrix are added to the inside of the Type I or Type II hollow fibers by pipetting the porous matrix and cells into the lumen of a fiber (approximately 2 cm in length). The fiber is filled up to about 1 mm from an open end. A solution of the same acrylic copolymer in DMSO is injected as a small drop into the open end of the fiber to form a sealed end of the fiber. The sealed end is further sealed by heating and then cooling in media the sealed end. Fibers can be stored in growth media.

Alternatively, porous growth matrix containing brown adipose cells or UCP-transfected cells can be placed into semipermeable tubular membranes or flat "tea bags" having a molecular weight cutoff of from about 10,000 daltons to about 50,000 daltons (W. R. Grace & Co.). The tubular membranes are washed in culture medium and the ends are sealed by heat followed by dipping in a solution of acrylic copolymer (e.g., XM casting solution Grace) similar to that used to make the semipermeable membranes.

The filled fibers can be injected or implanted into an individual to act as metabolism units to catabolize fatty acids. Co-administration of small amounts of heparin can facilitate hydrolysis of fatty acids from triglycerides to made fuel more readily available. Preferably, the pharmaceutical composition can be administered intraperitoneally. However, the pharmaceutical composition can also be administered subcutaneously, intramuscularly, or encapsulated cells can be injected into the portal vein. The rate of caloric consumption by the inventive pharmaceutical composition depends upon the amount of cultured brown adipose cell administered. Generally, every gram of pharmaceutical composition can metabolize 6.2 calories per day, which translates to about 0.81 grams of fat per day.

The Extracorporeal Device

The extracorporeal device comprises a hollow membrane chamber having a molecular weight cutoff of at least 10,000 daltons (Amicon) and having an oxidizing component located on the first side of the membrane and circulating blood in contact with the second side of the membrane. The semipermeable membrane is located in a cell chamber allowing fluids to circulate through a first chamber in contact with the first side of the semipermeable membrane and a second chamber allowing blood to circulate through and contact the second side of the semipermeable membrane. Preferably there are a plurality of semipermeable membrane devices located within a cell chamber to maximize contact of circulating blood with semipermeable membrane. Such a dual chambered device comprising a semipermeable membrane is similar to the hollow membrane chamber used in kidney dialysis machines. The first chamber is filled with brown adipose cells or UCP-transfected cells in a porous growth matrix as described herein. The cells are maintained, when not in use, with culture medium circulating across the semipermeable membrane through the second chamber. When in use, blood from an individual is circulated across the second chamber. A small dose of heparin 1200–2500 IU/hr. is added to the circulating blood to prevent thrombi formation and to assist hydrolysis of fatty acids from triglycerides in the circulation blood. The mechanics of blood circulation and pumping to and from the patient is similar to devices currently used for kidney dialysis treatment.

The rate of catabolism of fatty acids depends upon the metabolic state and activation of the brown adipose cells or UCP-transfected cells in the first chamber. While in use, metabolic rates can be increased in confluent cultures of cells by infusing Norepinephrine (NE) (about 0.1 μM) into the first chamber. NE will remain in and be consumed in the first chamber and not migrate to the patient via the second chamber. Further, NE can activate transcription of a fat-specific uncoupling protein called thermogenin (UCP). UCP expression was maximal when confluent culture brown adipose cells are activated with NE (Rehnmark et al., *J. Biol. Chem.* 265:16464, 1990).

It is also possible to promote hydrolysis of fatty acids from circulating triglycerides in the second chamber by immobilizing and embedding a lipase enzyme within the semipermeable membrane. An example of a lipase enzyme is lipoprotein lipase (E.C. 3.1.1.3). A method for immobilizing an enzyme in a semipermeable membrane is described in Kitano and Ise, *Trends Biochem.* 2:5, 1984. Briefly, a dry semipermeable membrane is dipped into an aqueous solution containing the lipase enzyme. Enzyme is absorbed into the spongy lumen where is remains to hydrolyze triglycerides into fatty acids wherein the fatty acids can freely diffuse across the semipermeable membrane.

The following examples are designed to illustrate the present invention.

EXAMPLE 1

This example illustrates manufacture of a pharmaceutical composition of the present invention. Brown fat precursor cells are isolated from interscapular brown adipose tissue of 20–25 day old Sprague-Dawley rats in an isolation buffer. Isolation buffer is made with 123 mM NaCl 5 mM KCl, 1.3 mM $CaCl_2$, 5 mM glucose, 1.5% crude bovine serum albumin and 100 mM HEPES (adjust to pH 7.4 with NaOH), with 0.2% (w/v) collagenase and sterile filtered through 0.45 μm and 0.22 μm membranes just before use. The rats are killed by cervical dislocation, and interscapular brown adipose tissue is dissected out under sterile conditions. The tissue is cut into small pieces and incubated in isolation buffer in siliconized glass vials for 30 min at 37° C. in a shaking water bath. The vials are vortexed every five minutes.

Tissue remnants are removed by filtering the tissue through a 250 μm nylon screen into plastic test tubes. The test tubes are left undisturbed for 30 min to allow mature adipocytes and fat droplets from broken cells to float. The infranatant is collected through a needle and filtered through a 25 μm nylon screen to remove cell aggregates. Brown adipose cells are pelleted by centrifugation (700×g for 10 min) and resuspended in culture medium. Culture medium is Dulbecco's modified Eagle's medium supplemented with 10% newborn calf serum, 4 nM insulin, 10 mM HEPES, antibiotics (50 IU penicillin, 50 μg streptomycin), and 25 μg of sodium ascorbate per ml of medium. Brown adipose cells are inoculated at a density of $0.5 \times 10^6$ cells per 75 mm petri dish containing 5 ml of culture medium.

Brown adipose cells are grown at 37° C. in 8% $CO_2$ in air at 80% humidity. The medium is changed on days 1 and 3 and every other day thereafter until the cells reach confluence (about 6 to 10 days). After confluency, the cells detach and float in a monolayer in the petri dish.

Two pieces of flat permselective membrane of at least 10,000 dalton molecular weight cutoff (W. R. Grace & Co.) are placed under and over this layer of cells. The membrane is sutured around the edges to form a completely sealed bag (i.e., a "tea bag"). The tea bag is stored submerged in culture medium at 37° C. in 8% $CO_2$ in air at 80% humidity until it is ready for norepinephrine treatment and implantation.

Alternatively, or in addition, other brown adipose cells are collected before they spontaneously detach. Culture media is aspirated from the petri dish and cells are incubated in 3 ml of isolation buffer in a shaking water bath at 37° C. for 5 min. Petri dishes are washed with an additional 3 ml of isolation buffer, combined with the first aspirate, and centrifuged at 400 g for 10 min. The cell pellet is washed with an additional 4 ml of culture medium to collect detached brown adipose cells. The cells are suspended in a solution of 1% (w/v) sodium alginate in phosphate buffered saline (PBS). This suspension is drawn into a syringe and injected into a semipermeable tubular membrane (3 cm×2.0 mm i.d. with a 50,000 to 80,000 molecular weight cutoff, W. R. Grace & Co.). The ends of the tubular membrane are sealed by dipping the ends into a 12.5% (w/w) solution of poly-(acrylonitrile-co-vinyl chloride) in dimethyl sulfoxide and then touching it with a heated metal spatula. The sealed tubular membranes are placed in a solution of $CaCl_2$ for 6 minutes to cross-link the alginate. These pharmaceutical compositions are kept in culture medium at 37° C. in 8% $CO_2$ in air at 80% humidity until ready for norepinephrine treatment and implantation.

Thermogenin expression is stimulated in the encapsulated brown adipose cells by adding norepinephrine to the hollow fiber or tea bag encapsulated brown adipose cell cultures at a concentration of 0.1 µM and incubating in culture medium for at least four hours. The hollow fiber or tea bag of brown adipose cells is ready for implantation.

EXAMPLE 2

This example illustrates administration of the pharmaceutical composition of Example 1 to Zucker rats to effect weight loss without significant loss of muscle mass. Fa/fa genetically obese Zucker rats are a well studied animal model for obesity and brown fat metabolism. Development of obesity in Zucker rats is believed to be due to attenuated energy expenditure and contributed by defective brown adipose tissue-mediated thermogenesis. Therefore, Zucker rats are an appropriate animal model to study hypermetabolic therapy to effect weight loss.

Fa/fa Zucker rats are anesthetized by ether inhalation. From one to four tea bags (1 to 4 g/rat) from Example 1 are inserted into the peritoneal cavity through a midline incision. The incision is closed with 2 layers of 4-0 silk suture. After implantation, the weight of each rat is carefully monitored and compared with sham-implanted control animals. Other rats are similarly implanted with (6–10/rat) hollow fiber cultured brown adipose cells (according to Example 1) or empty control hollow fibers. The weight of these animals is carefully monitored and compared to the control animals.

I claim:

1. A pharmaceutical composition for reducing body fat content comprising a culture of brown adipose cells encapsulated in a semipermeable membrane, wherein the semipermeable membrane has a molecular weight cutoff of at least 10,000 daltons.

2. The pharmaceutical composition of claim 1 wherein the semipermeable membrane comprises a tubular membrane having two ends, filled with the culture of brown adipose cells and sealed at both ends.

3. The pharmaceutical composition of claim 1 wherein the semipermeable membrane is an acrylic copolymer.

4. The pharmaceutical coinposition of claim 1 wherein the semipermeable membrane comprises a sealed bag.

5. The pharmaceutical composition of claim 1 wherein the culture of brown fat cells is comprised a porous growth matrix.

6. The pharmaceutical composition of claim 5 wherein the porous growth matrix comprises calcium alginate beads.

7. The pharmaceutical composition of claim 1 wherein the semipermeable membrane comprises a lipoprotein lipase.

8. A method of oxidizing calories to reduce body fat content in a patient in need thereof comprising parenterally administering or implanting the pharmaceutical composition of claim 1.

9. The method of claim 8 wherein the route of administration of the pharmaceutical composition is by subcutaneous injection, intramuscular injection, intraperitoneal injection, intraportal implantation or intraportal injection.

* * * * *